United States Patent
Katzman

(12)
(10) Patent No.: US 6,235,042 B1
(45) Date of Patent: May 22, 2001

(54) ATHERECTOMY DEVICE

(75) Inventor: Youval Katzman, Zichron Yaacov (IL)

(73) Assignee: Arteria Medical Science, Inc., San Francisoc, CA (US)

( * ) Notice: Subject to any disclaimer, the term of this patent is extended or adjusted under 35 U.S.C. 154(b) by 0 days.

(21) Appl. No.: 09/447,450

(22) Filed: Nov. 22, 1999

Related U.S. Application Data

(63) Continuation-in-part of application No. 09/158,038, filed on Sep. 21, 1998, now Pat. No. 6,019,772.

(51) Int. Cl.[7] .................................................. A61B 17/32
(52) U.S. Cl. ............................................................ 606/159
(58) Field of Search .................................. 606/159, 170, 606/167, 180, 171, 176; 604/22

(56) References Cited

U.S. PATENT DOCUMENTS

| | | | |
|---|---|---|---|
| 4,020,847 | 5/1977 | Clark, III | 606/159 |
| 4,979,951 | 12/1990 | Simpson | 606/159 |
| 5,282,484 | 2/1994 | Reger | 606/159 |
| 5,366,464 | 11/1994 | Belknap | 128/305 |
| 5,584,843 | 12/1996 | Wulfman et al. | 606/159 |
| 5,695,506 | * 12/1997 | Pike et al. | 606/159 |
| 5,779,721 | * 7/1998 | Nash | 606/159 |
| 6,019,772 | * 2/2000 | Shefaram et al. | 606/159 |

* cited by examiner

*Primary Examiner*—Kevin Truong
(74) *Attorney, Agent, or Firm*—Fish & Neave; Nicola A. Pisano

(57) ABSTRACT

An atherectomy device is provided wherein a catheter has a cutting region including plurality of slotted tubular members interconnected by flexible segments. Each slotted tubular member includes cutting edges that sever occlusive material from the interior of a vessel when the cutting region is rotated. The flexible segments may be formed by cutting windows in a tapered hollow tubular member, or may comprise bellows-shaped tubes or helical coils, or may comprise one or more tubular segments and may include a lumen that allows suction to be drawn through the device, or to permit the delivery of contrast agents, dyes, fluids or drugs to the operative site. A guide catheter also may be provided for positioning the cutting region of the atherectomy device at the operative site.

22 Claims, 5 Drawing Sheets

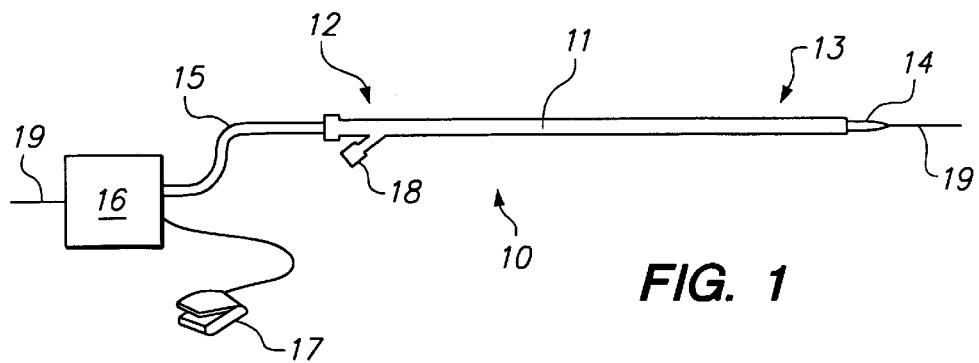
FIG. 1
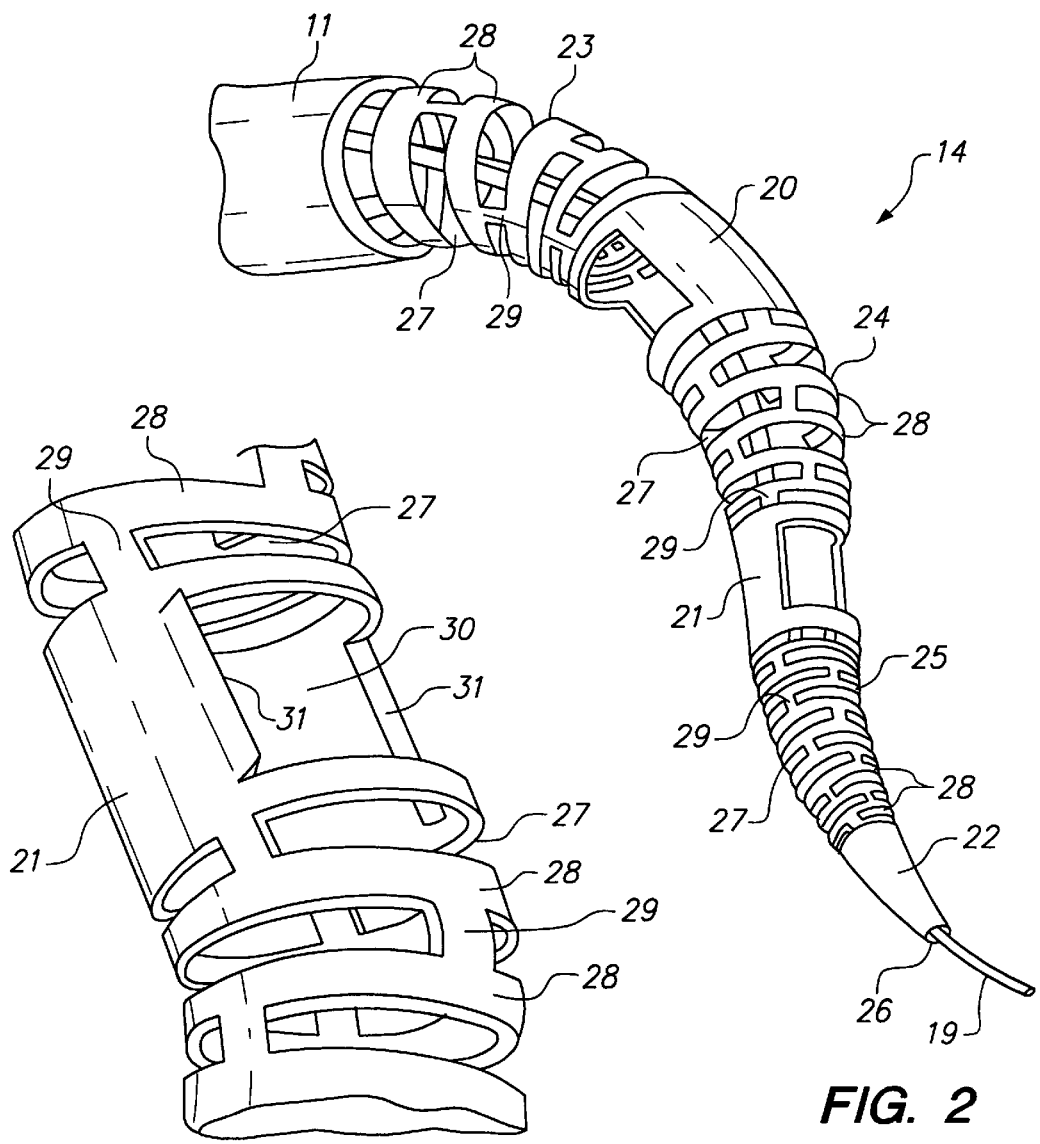
FIG. 2
FIG. 3

ATHERECTOMY DEVICE

RELATED APPLICATION

This application is a continuation-in-part of commonly assigned application Ser. No. 09/158,038, filed Sep. 21, 1998 now U.S. Pat. No. 6,019,722.

FIELD OF THE INVENTION

The present invention relates to apparatus for removing occlusive material from the interior of a vessel or stent to restore bloodflow therethrough.

BACKGROUND OF THE INVENTION

A number of atherectomy devices have been developed to remove occlusive material, such as plaque and cellular overgrowths, from the interior of a vessel to restore blood flow through the vessel. While many of these previously known devices have been widely accepted for use in interventional procedures, such devices continue to have drawbacks that limit the applicability of the devices in certain circumstances.

U.S. Pat. No. 4,979,951 to Simpson describes a device wherein a distal region carries a housing having an elongated slot. A cutting member disposed within the housing reciprocates past the slot to sever material protruding into the housing. A drawback of the Simpson device is that it is useful only in arteries large enough to accommodate the housing. In addition, that device cannot be used to remove occlusive material from the walls of tortuous vessels, because the device is incapable of conforming adequately to a curved vessel wall.

U.S. Pat. No. 5,366,464 to Belknap describes an atherectomy device formed from a tapered helical coil covered with a polymeric sheath. A plurality of elongated slots are formed in the helical coil so that the severed ends of adjacent turns of the coil form a flexible cutting edge. While the Belknap device offers the advantages of conforming to tortuous anatomy, and being able to access smaller vessels, it has been determined that the device is prone to failure during use. Specifically, the sheath material in the vicinity of the windows is incapable of sustaining the high torque loads imposed during operation of the device.

U.S. Pat. No. 4,020,847 to Clark describes a rotating cutter device including a slotted cylindrical member disposed at the end of a helical coil. The length of the slotted cylindrical member may make it difficult for the device to pass through or remove occlusive material in tortuous anatomy, or to insert the cutting device into smaller arteries.

In view of the foregoing, it would be desirable to provide an atherectomy device that permits occlusive material to be removed from tortuous and small diameter vessels, and which overcomes the disadvantages of previously known devices.

It further would be desirable to provide an atherectomy device capable of being configured to excise occlusive material from tapered arteries.

It still further would be desirable to provide an atherectomy device that enables occlusive material to be removed from vessels having a tortuous anatomy.

SUMMARY OF THE INVENTION

In view of the foregoing, it is an object of this invention to provide an atherectomy device that permits occlusive material to be removed from tortuous and small diameter vessels, and which overcomes the disadvantages of previously known devices.

It is another object of the present invention to provide an atherectomy device capable of being configured to excise occlusive material from tapered arteries.

It is a further object of this invention to provide an atherectomy device that enables occlusive material to be removed from vessels having a tortuous anatomy.

These and other objects of the present invention are accomplished by providing an atherectomy device comprising a catheter having a cutting region including plurality of slotted tubular members interconnected by flexible segments. Each slotted tubular member includes cutting edges that sever occlusive material from the interior of a vessel when the cutting region is rotated. The flexible segments may be formed by cutting windows in a tapered hollow tubular member, or may comprise bellows-shaped tubes or helical coils. Alternatively, flexible segments may be formed by linking together a plurality of individual tubular segments using a hinge-like structure that may be freely angularly displaced. The flexible segments may be coated with a flexible polymeric material to allow suction to be drawn through the device, or to permit the delivery of contrast agents, dyes, fluids or drugs to the operative site. A guide catheter may be used for positioning the cutting region of the atherectomy device at the operative site.

BRIEF DESCRIPTION OF THE DRAWINGS

Further features of the invention, its nature and various advantages will be more apparent from the accompanying drawings and the following detailed description of the preferred embodiments, in which:

FIG. 1 is a perspective view of an illustrative embodiment of an atherectomy device constructed in accordance with the principles of the present invention;

FIG. 2 is a detailed perspective view of the cutting region of the atherectomy device of FIG. 1;

FIG. 3 is a further detailed perspective view of the slotted tubular member of the cutting region of FIG. 2;

DETAILED DESCRIPTION OF THE INVENTION

Figures 4, 5:
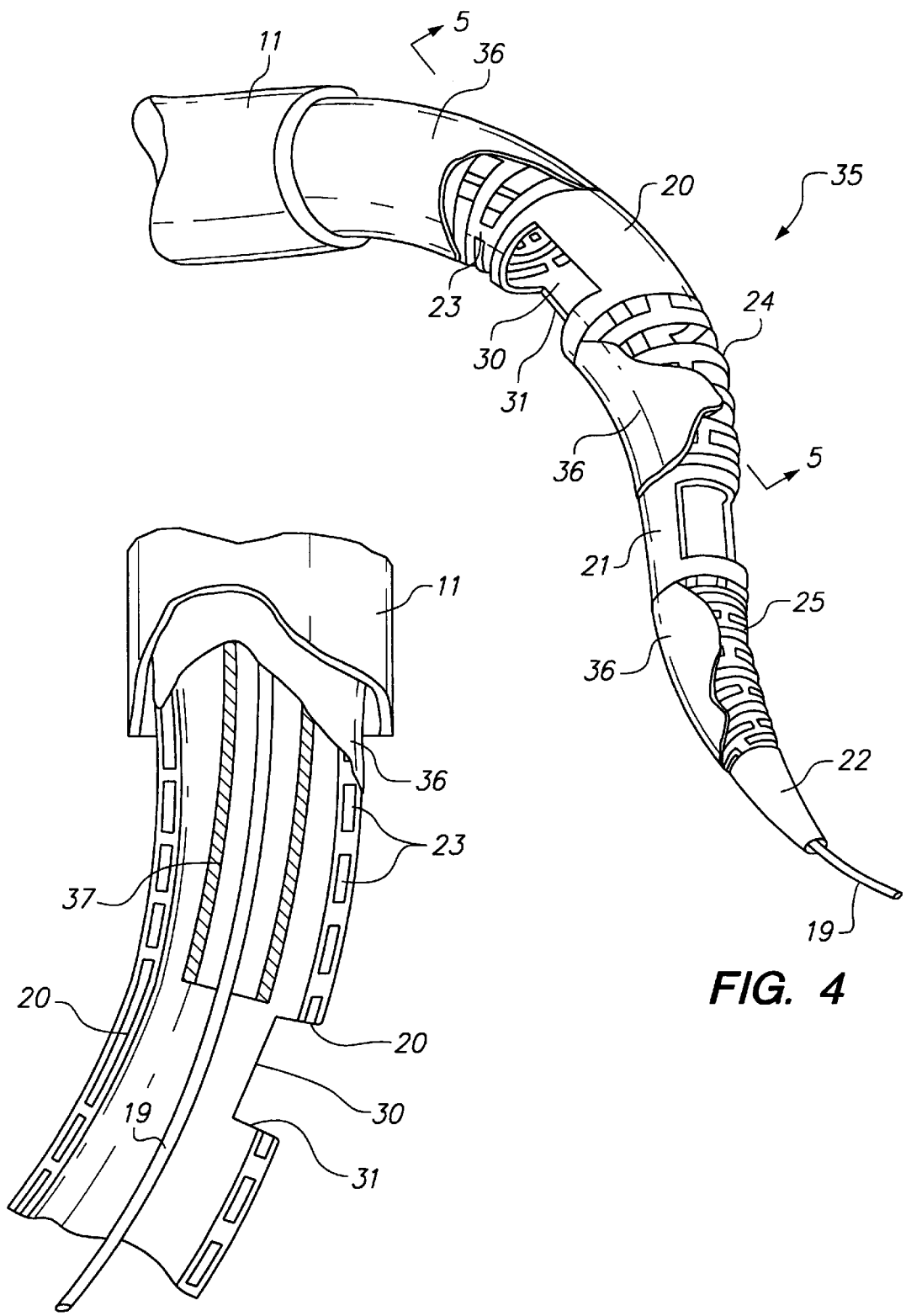
FIG. 4 is a detailed perspective view of the cutting region of an alternative embodiment of an atherectomy device of the present invention.
FIG. 5 is a detailed side sectional view of the cutting region of FIG. 4 taken along view line 5—5 of FIG. 4.
Figure 6:
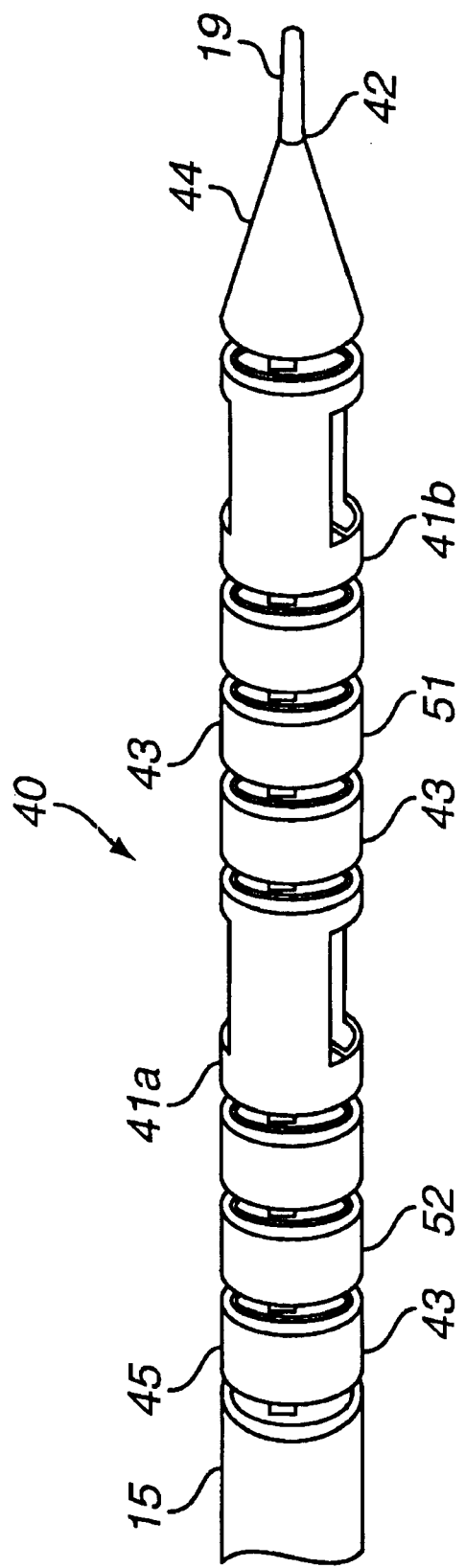
FIG. 6 is a detailed perspective view of the cutting region of another alternative embodiment of an atherectomy device of the present invention.

The present invention provides an atherectomy device capable of negotiating and removing plaque from curved and tapered vessels, without suffering from the drawbacks of previously known devices. More particularly, an atherectomy device constructed in accordance with the principles of the present invention comprises two or more slotted tubular members connected by flexible tubular segments, so that the slotted tubular members may pass through, and sever occlusive material from, tortuous vessels. In addition, the flexible segments may be tapered to permit a cutting region of the atherectomy device to be advanced to remove occlusive material from tapered vessels.

Referring now to FIG. 1, a first illustrative embodiment of an atherectomy device constructed in accordance with the principles of the present invention is described. Device 10 comprises hollow guide catheter 11 having proximal end 12 and distal end 13. Flexible cutting region 14 extends from distal end 13 of catheter 11, and is coupled via flexible drive cable 15 to controller 16. Controller 16 comprises a motor and circuitry, actuated by footpedal 17, that rotates and/or longitudinally reciprocates drive cable 15 and cutting region 14, as is per se known. Controller 16 may be configured as described, for example, in U.S. Pat. No. 5,366,464 to Belknap, which is incorporated herein by reference.

Catheter 11 may include one or more ports 18 for inducing suction to aspirate severed material from the operative site, as described hereinbelow. Drive cable 15 and flexible cutting region 14 preferably include a central lumen that accepts guide wire 19, to assist in percutaneously and transluminally inserting atherectomy device 10. Drive cable 15 may comprise, for example, a helical metal wire coil. Drive cable 15 preferably is coupled to cutting region 14 at a position within guide catheter 11, proximal of distal end 13, and is capable of transmitting rotation, and optionally, reciprocating motion, to cutting region 14.

Referring now to FIGS. 2 and 3, cutting region 14 is described, and includes tubular members 20 and 21 and tip 22 interconnected by flexible segments 23, 24 and 25. Flexible segment 23 is coupled at its proximal end, for example, by welding, friction fit, or threads, to a distal end of drive cable 15, and at its distal end to tubular member 20. Flexible segment 24 couples tubular member 20 to tubular member 21, and flexible segment 25 couples tubular member 21 to tip 22. Tip 22 includes aperture 26 through which guide wire 19 passes.

Each of flexible segments 23–25 comprises a tube, preferably tapered, in which windows 27 have been cut, for example, by chemical etching, or laser or electron beam cutting, to create a flexible lattice of hoops 28 interconnected by cross-members 29. Flexible segments 23–25 may be integrally formed with tubular members 20 and 21 and tip 22, or may be separately formed and joined by techniques per se known. Applicant has determined that by adjusting the wall thickness and length of the flexible segments and tubular members, the area of windows 27 and the number of cross-members 29, a flexible segment having a desired degree of strength and flexibility may be obtained. Alternatively, flexible segments 23–25 may comprise sections of helical coil or bellows-shaped tube.

Tubular members 20 and 21, and tip 22, may be separately formed and coupled by conventional techniques, e.g., welding, threads, friction fit, etc., between flexible segments 23–25, or may be integrally formed with flexible segments 23–25. Each of tubular members 20 and 21 is formed from a single-piece hollow tube by cutting slots 30 that extend for a portion of the circumference of the tubular member, and include sharpened cutting edges 31. Cutting edges 31 also may be formed to extend beyond the exterior surface of the tubular member, as shown in FIG. 3, to provide device 10 with a cutting diameter larger than that of the tubular member. Each tubular member 20 and 21 may have a uniform diameter, or may be tapered from one end to the other to match the diameters of the flexible segments to which the tubular member is coupled.

Guide catheter 11 may comprise a material typically used in catheter construction, such as polyethylene, polypropylene or urethane. Flexible segments 23–25, tubular members 20 and 21, and tip 22 preferably are formed from a high strength metal or metal alloy, such as stainless steel or nickel titanium. Alternatively, high strength plastic materials may be used for some or all of these components. Flexible segments 23–25 also may comprise metal, metal alloy or high strength plastic tapered helical coil sections.

In accordance with the principles of the present invention, the relative lengths of the tubular members and the flexible segments may be selected so that cutting region 14 is capable of bending within, and therefore removing occlusive material from, a vessel having a predetermined radius. In particular, previously known atherectomy devices such as described in the above-mentioned patents to Simpson and Clark are impracticable to use in curved vessels. The present invention, however, enables a series of relatively short tubular members, interconnected by short flexible segments, to be assembled that provides a very flexible device.

With respect to FIGS. 4 and 5, an alternative embodiment of the atherectomy device of the present invention is described. Atherectomy device 35 is constructed as described above for the embodiment of FIG. 1. In addition, the components of the cutting region, except slots 30 and cutting edges 31, include cover 36 comprising a flexible plastic or elastomeric material, such as polyethylene, urethane, or nylon. Cover 36 also may be impregnated with or coated with a lubricious material, such as polytetrafluoroethylene, to reduce abrasion of the vessel walls in the areas not contacted by cutting edges 31.

In FIG. 5, atherectomy device 35 includes lumen 37, which may be coupled by suitable means to port 18 of guide catheter 11. Lumen 37 may comprise a tube formed of materials typically used in catheter construction, and may be used to aspirate severed material from the operative site, to inject contrast agents, dyes, fluids (e.g., saline), or drugs to the operative site, or combinations thereof.

Referring now to FIGS. 6–9, an alternative embodiment of the atherectomy device of the present invention is described. Atherectomy device 40 is constructed as described above for the embodiment of FIG. 1. Atherectomy device 40 includes first and second tubular members 41a and 41b, respectively, flexible segments 51 and 52 each comprised of a plurality of tubular segments 43, and tip 44. Tip 44 couples to the distal end of second tubular member 41b, and includes aperture 42 through which guide wire 19 passes.

Tubular segments 43 connect to one another to form flexible segments 51 and 52. Flexible segment 51 connects first and second tubular members 41a and 41b. Flexible segment 52 couples at its proximal end, for example by welding, friction fit, or threads, to a distal end of drive cable 15, and connects at its distal end to a proximal end of first tubular member 41a.

Tubular segments 43 and first and second tubular members 41a and 41b transmit torque and conform to the tortuosity of curved vessels without exerting bending forces on the vessel walls. Specifically, because tubular segments 43 are connected by freely moveable structures that act as hinges, no continuous bending force is required to retain a give angular relationship between successive elements.

Consequently, the segments freely conform to vessel tortuosity without imposing a counteracting bending force on the vessel wall. As a result, atherectomy device 40 requires less insertion force than previously known atherectomy devices.

Figure 7:
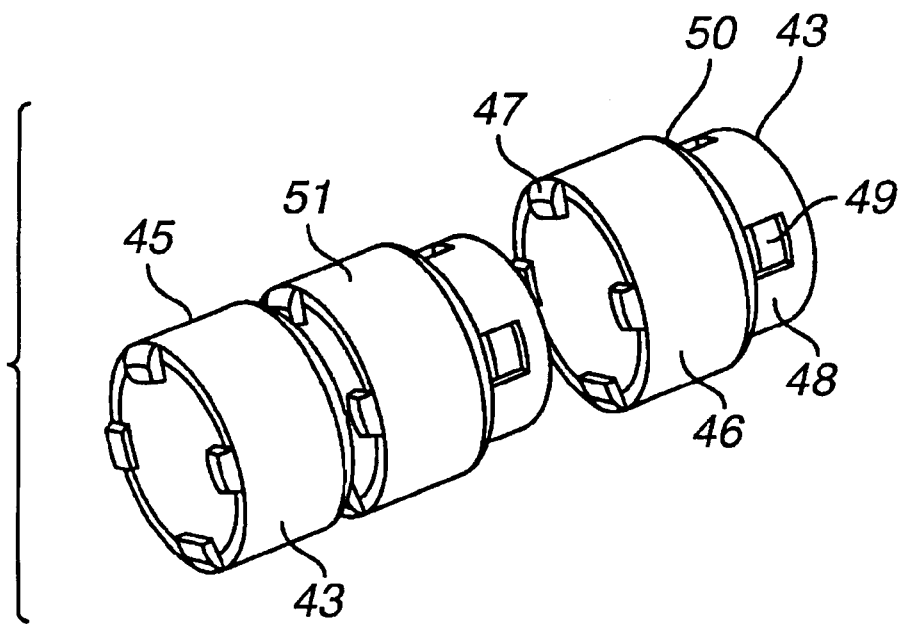
FIG. 7 is a further detailed perspective view of tubular segments of the cutting region of FIG. 6.

As shown in FIG. 7, each of tubular segments 43 comprises first tubular portion 46 having first diameter $D_1$ and hinge portions 47 (illustratively tabs), second tubular portion 48 having second diameter $D_2$, narrower than the first diameter, hinge portions 49 (illustratively holes or indents), and tapered section 50 coupling first tubular portion 46 to second tubular portion 48. Tubular segments 43 may be formed from a single-piece hollow tube by cutting slots in one end of the tube, for example by chemical etching, or laser or electron beam cutting, to form hinge portions 47 that are then crimped radially inward from exterior surface 51 of the tube. Hinge portions 49 then may be cut in the other end of the tube, for example by chemical etching, or laser or electron beam cutting. Finally, tapered section 50 may be formed, for example by swaging the tube, to narrow the diameter of second tubular portion 48.

Still referring to FIG. 7, a plurality of tubular segments 43 may be flexibly linked together to form flexible segments 51 and 52. In particular, hinge portions 47 in first portion 46 of one tubular segment 43 align with and may be flexibly engaged with hinge portions 49 in second tubular portion 48 of preceding tubular segment 43, hinge portions 47 and 49 forming hinge-like structures that may be readily angularly displaced without continued application of a bending force. For example, hinge portions 47 may snap into hinge portions 49 to flexibly link two tubular segments. A plurality of tubular segments 43 therefore may be so linked to form flexible segments 51 and 52. Although three tubular segments 43 are shown flexibly linked in FIG. 7, a greater or fewer number of tubular segments may be so linked.

Figure 8:
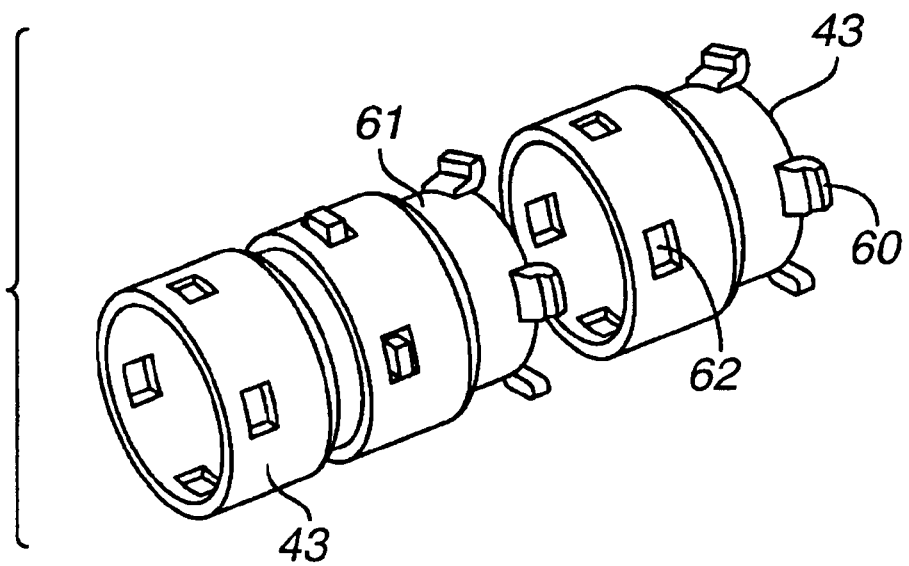
FIG. 8 is an further detailed perspective view of an alternative embodiment of tubular segments of the cutting region of FIG. 6.

As shown in FIG. 8, tubular segments 43 alternatively may be formed from a single-piece hollow tube by cutting slots in one end of the tube to form hinge portions 60 that are then crimped radially outward from exterior surface 61 of the tube. Hinge portions 62 then may be cut in the other end of the tube. To link tubular segments 43 together, hinge portions 60 of one tubular segment 43 align with and may be flexibly engaged with hinge portions 62 in succeeding tubular segment 43. Although three tubular segments 43 are shown flexibly linked in FIG. 9, a greater or fewer number of tubular segments may be so linked.

Figure 9:
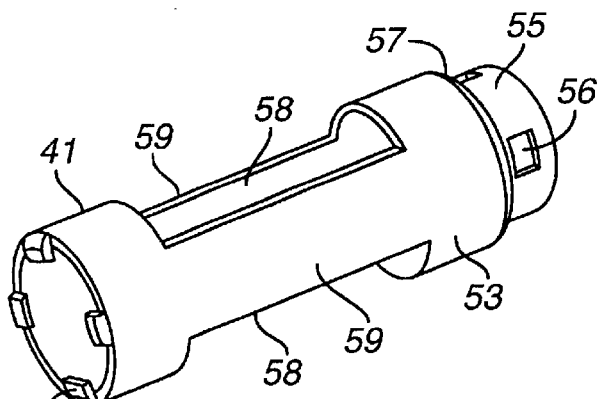
FIG. 9 is a further detailed perspective view of a tubular member of the cutting region of FIG. 6.

As shown in FIG. 9, first and second tubular members 41a and 41b each comprise first tubular portion 53 having hinge portions 54 and slots 58, second tubular portion 55 having hinge portions 56, and tapered section 57 coupling the first and second tubular portions. Hinge portions 54 align with and may be flexibly engaged with hinge portions 49 of a proximally-located tubular segment 43, and hinge portions 47 of a distally-located tubular segment 43 align with and may be flexibly engaged with hinge portions 56. It will of course be appreciated that first tubular portion 53 alternatively may include hinge portions 56, and second tubular portion 55 alternatively may include hinge portions 54.

Hinge portions 47 and 49, and 60 and 62 may take any of a number of forms. For example, the hinge portions may comprise circumferential ridges that engage corresponding recesses in adjacent tubular segments. Alternatively, tubular segments may have tabs at either end, with alternating tubular segments having holes or indents at either end. Other combinations also are possible, as long as adjacent tubular segments have hinge portions that freely interengage. Similarly, hinge portions 54 and 56 may take any of a number of forms, as long as the hinge portions freely interengage with the hinge portions of adjacent tubular segments.

Referring again to FIG. 9, first tubular portion 53 also includes slots 58 that extend partially around the circumference of the tubular member, and include sharpened cutting edges 59. Cutting edges 59 also may be formed to extend beyond the exterior surface of the tubular member to provide device 10 with a cutting diameter larger than that of the tubular member. First and second tubular members 41a and 41b may be formed from a single-piece hollow tube similar to tubular segments 43, described above, and by additionally cutting slots 58 in first portion 53.

First and second tubular members 41a and 41b and tubular segments 43 preferably are formed from a high-strength metal or metal alloy, such as stainless steel or nickel titanium. Alternatively, first and second tubular members 41a and 41b and tubular segments 43 may be formed from high strength plastic materials.

Figure 10:
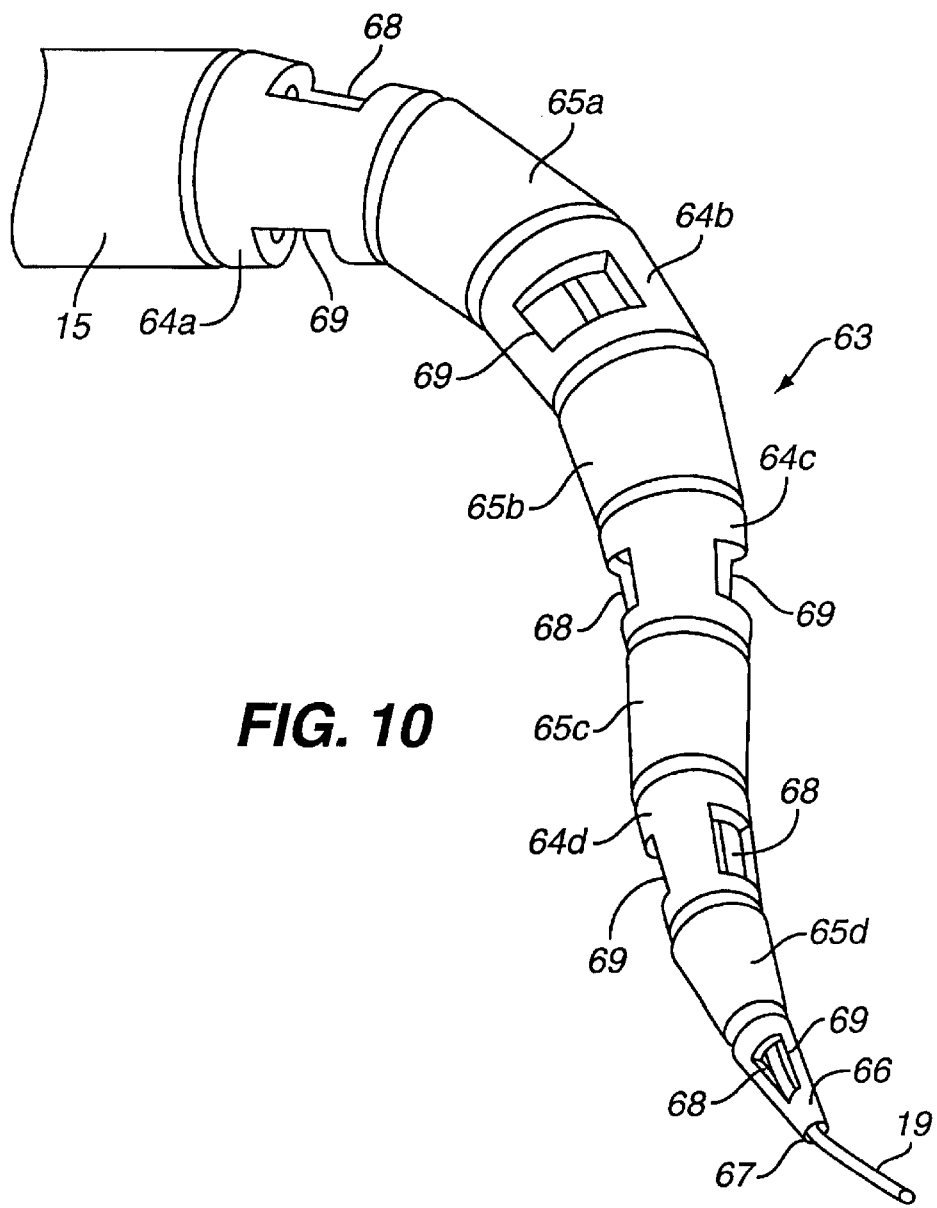
FIG. 10 is a detailed perspective view of the cutting region of still another alternative embodiment of an atherectomy device of the present invention.

Referring now to FIG. 10, another alternative embodiment of the atherectomy device of the present invention is described. Atherectomy device 63 is constructed as described above for the embodiment of FIG. 1. Atherectomy device 63 includes tapered tubular members 64a–64d, tapered tubular segments 65a–65d, and tapered tip 66. Tapered tip 66 couples to the distal end of tapered tubular segment 65d, and includes aperture 67 through which guide wire 19 passes.

Although not shown in FIG. 10, similar to tubular segments 43 (described above) each of tapered tubular members 64a–64d and tapered tubular segments 65a–65d comprise first and second portions having hinge portions that permit tapered tubular members 64a–64d and tapered tubular segments 65a–65d to be flexibly linked together.

Additionally, tapered tubular members 64a–64d and tapered tubular segments 65a–65d may be formed from a single-piece tapered hollow tube by cutting slots in one end of the tube, for example by chemical etching, or laser or electron beam cutting, to form hinge portions that are then crimped radially inward (or outward) from the exterior surface of the tube. Hinge portions then may be cut in the other end of the tube, for example by chemical etching, or laser or electron beam cutting. Finally, the tapered section may be formed, for example by swaging the tube, to narrow the diameter of the second portion.

Tapered tubular members 64a–64d and tapered tip 66 include slots 68 that extend partially around the circumference of the tapered tubular member and tapered tip, and include sharpened cutting edges 69. Cutting edges 69 also may be formed to extend beyond the exterior surface of the tubular member to provide device 10 with a cutting diameter larger than that of the tubular member.

Tapered tubular segments 65a–65d connect tapered tubular members 64a–64d to one another. As shown in FIG. 10, tapered tubular segment 65a connects tapered tubular members 64a and 64b, tapered tubular segment 65b connects tapered tubular members 64b and 64c, tapered tubular segment 65c connects tapered tubular members 64c and 64d, and tapered tubular segment 65d connects tapered tubular member 64d to tapered tip 66. Tapered tubular segment 64a couples at its proximal end, for example by welding, friction fit, or threads, to a distal end of drive cable 15.

Tapered tubular segments 65a–65d may be connected together to form chains of flexible segments (similar to flexible segments 51 and 52 in FIG. 6) that are used to connect tapered tubular members. Additionally, as with atherectomy device 40, tapered tubular members 64a–64d and tapered tubular segments 65a–65d transmit torque and conform to the tortuosity of curved vessels without exerting bending forces on the vessel walls.

Tapered tubular members 64a–64d and tapered tubular segments 65a–65d preferably are formed from a high-strength metal or metal alloy, such as stainless steel or nickel titanium. Alternatively, tapered tubular members 64a–64d and tapered tubular segments 65a–65d may be formed from high strength plastic materials.

Although preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed is:

1. An atherectomy device comprising:

a drive cable;

a tubular member having a first and second hinge portions on each end of the tubular member, a portion defining a slot between the first and second hinge portions, and a cutting edge disposed along the slot, wherein the slot is less than the full radial circumference of the tubular member; and a plurality of tubular segments, each tubular segment comprising a first portion that has a first hinge portion and a second portion that has a second hinge portion, wherein the tubular member and the tubular segments are flexibly connected together at the hinge portions to form a chain that is coupled to the drive cable, a first tubular segment being coupled to the first hinge portion of the tubular member and a second tubular segment coupled to the second hinge portion of the tubular member, the chain being movable relative to the drive cable without exerting a bending force therebetween.

2. The atherectomy device of claim 1, wherein the first portion of the first tubular segment has a first diameter and the second portion of the second tubular segment has a second diameter different from the first diameter.

3. The atherectomy device of claim 2, wherein the first diameter is larger than the second diameter.

4. The atherectomy device of claim 2, wherein the first diameter is smaller than the second diameter.

5. The atherectomy device of claim 1, wherein the tubular member further comprises a tapered exterior surface.

6. The atherectomy device of claim 1 further comprising a guide catheter having a lumen and a distal end, wherein the drive cable is disposed in the lumen and the link extends beyond the distal end.

7. The atherectomy device of claim 1 further comprising a lumen configured for aspirating occlusive material severed by the cutting edges of the tubular member.

8. The atherectomy device of claim 1 further comprising a lumen configured for injecting a contrast agent, dye, fluid or drug.

9. The atherectomy device of claim 1 wherein the tubular member has an exterior diameter and the cutting edge of the tubular member extends beyond the exterior diameter.

10. The atherectomy device of claim 1 wherein the drive cable is configured to transmit rotational motion to the chain.

11. The atherectomy device of claim 1 wherein the drive cable is configured to transmit reciprocatory motion to the chain.

12. An atherectomy device comprising:

a drive cable;

a plurality of tubular members, each having a first and second hinge portions on each end of the tubular members, a portion defining a slot between the first and second hinge portions, and a cutting edge disposed along the slot, wherein the slot is less than the full radial circumference of the tubular member; and a plurality of tubular segments, each of the segments including a first portion having a first hinge portion and a second portion having a second hinge portion, wherein the tubular members and the tubular segments are flexibly connected together at the hinge portions to form a chain, the chain being cooperatively coupled to the drive cable to transmit torque between the drive cable and the tubular members without exerting a bending force therebetween.

13. The atherectomy device of claim 12, wherein the first portion of the tubular segments has a first diameter and the second portion of the tubular segments has a second diameter different from the first diameter.

14. The atherectomy device of claim 13 wherein the first diameter is larger than the second diameter.

15. The atherectomy device of claim 13, wherein the first diameter is smaller than the second diameter.

16. The atherectomy device of claim 12, wherein a first one of the tubular members further comprises a tapered exterior surface.

17. The atherectomy device of claim 12 further comprising a guide catheter having a lumen and a distal end, wherein the drive cable is disposed in the lumen.

18. The atherectomy device of claim 12 further comprising a lumen configured for aspirating occlusive material severed by the cutting edges of the tubular members.

19. The atherectomy device of claim 12 further comprising a lumen configured for injecting a contrast agent, dye, fluid or drug.

20. The atherectomy device of claim 12 wherein at least one of the tubular members has an exterior surface and the cutting edge of the tubular member extends beyond the exterior surface.

21. The atherectomy device of claim 12 wherein the drive cable is configured to transmit rotational motion to the chain.

22. The atherectomy device of claim 12 wherein the drive cable is configured to transmit reciprocatory motion to the chain.

* * * * *